(12) United States Patent
Smith et al.

(10) Patent No.: US 9,791,265 B2
(45) Date of Patent: Oct. 17, 2017

(54) METHODS OF DETERMINING THE SHAPE OF A SESSILE DROP

(71) Applicant: University of North Carolina at Charlotte, Charlotte, NC (US)

(72) Inventors: Stuart T. Smith, Charlotte, NC (US); Jacob W. Chesna, Alden, NY (US); Tsing-Hua Her, Charlotte, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 14/894,898

(22) PCT Filed: May 30, 2014

(86) PCT No.: PCT/US2014/040304
§ 371 (c)(1),
(2) Date: Nov. 30, 2015

(87) PCT Pub. No.: WO2014/194235
PCT Pub. Date: Dec. 4, 2014

(65) Prior Publication Data
US 2016/0123725 A1    May 5, 2016

Related U.S. Application Data

(60) Provisional application No. 61/829,662, filed on May 31, 2013.

(51) Int. Cl.
*G01B 11/24* (2006.01)
*G01N 13/00* (2006.01)

(52) U.S. Cl.
CPC ............ *G01B 11/24* (2013.01); *G01N 13/00* (2013.01)

(58) Field of Classification Search
CPC ......... G01B 11/24; G01N 13/00; F16K 31/02; F15D 1/00; B05C 5/02; B05C 11/1034
See application file for complete search history.

(56) References Cited

U.S. PATENT DOCUMENTS

| | | | |
|---|---|---|---|
| 4,820,281 A * | 4/1989 | Lawler, Jr. | G01F 3/00 604/253 |
| 4,936,828 A * | 6/1990 | Chiang | A61M 5/1689 604/253 |
| 5,542,289 A * | 8/1996 | Hool | G01N 13/02 324/691 |

(Continued)

OTHER PUBLICATIONS

Guena, G. et al., "Evaporation of sessile liquid droplets", Colloids and Surfaces A: Physicochemical and Engineering Aspects, vol. 291, Issue 1, pp. 191-196, Dec. 15, 2006.

(Continued)

*Primary Examiner* — Sang Nguyen
(74) *Attorney, Agent, or Firm* — Smith Moore Leatherwood LLP; J. Clinton Wimbish

(57) ABSTRACT

In one aspect, methods of determining the shape of a sessile drop are described herein. In some embodiments, a method described herein comprises measuring a first shape parameter of a sessile drop to obtain a first shape parameter value, measuring a second shape parameter of the drop to obtain a second shape parameter value, and using the first and second shape parameter values to calculate a third shape parameter value of a third shape parameter of the drop.

25 Claims, 18 Drawing Sheets

(56) References Cited

U.S. PATENT DOCUMENTS

| | | | |
|---|---|---|---|
| 6,700,656 B1* | 3/2004 | Chao | G01N 13/02 356/138 |
| 2002/0113839 A1* | 8/2002 | Hawkins | B41J 2/03 347/40 |
| 2004/0151828 A1* | 8/2004 | Zribi | B29D 11/00365 427/58 |
| 2006/0251797 A1* | 11/2006 | Erfle | B05C 5/02 427/8 |
| 2009/0198177 A1* | 8/2009 | Sawhney | A61B 17/0057 604/82 |
| 2009/0289213 A1* | 11/2009 | Pipper | B01J 20/28009 252/62.51 R |
| 2010/0277742 A1* | 11/2010 | McMillan | G01N 15/1463 356/450 |
| 2011/0093241 A1 | 4/2011 | Zhang et al. | |
| 2011/0131018 A1 | 6/2011 | Zhang et al. | |
| 2011/0305761 A1* | 12/2011 | Shum | A61K 9/1273 424/489 |
| 2012/0231489 A1 | 9/2012 | Lenhert | |
| 2012/0276334 A1 | 11/2012 | Fedynyshyn et al. | |
| 2014/0144518 A1* | 5/2014 | Bohringer | B01L 3/50273 137/13 |
| 2014/0318639 A1* | 10/2014 | Peret | F16K 31/02 137/386 |

OTHER PUBLICATIONS

International Search Report and Written Opinion issued in corresponding International Application No. PCT/US2014/040304, mailed Sep. 26, 2014, 9 pages.

\* cited by examiner

US 9,791,265 B2

METHODS OF DETERMINING THE SHAPE OF A SESSILE DROP

CROSS REFERENCE TO RELATED APPLICATION

This application is a U.S. National Phase of PCT/US2014/040304, filed May 30, 2014, which claims priority pursuant to 35 U.S.C. §119(e) to United States Provisional Patent Application Serial Number 61/829,662 filed May 31, 2013, both of which are incorporated by reference in their entireties.

FIELD

The present invention relates to methods of determining shape parameters of sessile drops and to methods of measuring the wettability of a surface.

BACKGROUND

Sessile drops can be present in a variety of material systems, and the shapes of the sessile drops can affect the performance characteristics of such systems. The shape of a sessile drop can also characterize the properties of a surface on which the drop is disposed. For example, in the case of a wetting system, the wettability of a surface can be characterized by the wetting contact angle of the drop.

One typical approach to measuring the shape of a sessile drop employs lateral measurement and/or visual inspection of the drop. Some contact angle goniometer systems, for instance, use an optical subsystem to create a visual representation of the sessile drop from the side. The image is then used to measure the wetting contact angle by visual inspection. Unfortunately, such approaches based on lateral measurement and/or visual inspection are inherently limited. In particular, techniques based on lateral measurement and/or visual inspection often cannot be used to determine the shape of a sessile drop having a small drop diameter, and/or in situations wherein an optical path from the measurement instrument to the profile of the sessile drop is obstructed. Therefore, there exists a need for improved methods of determining the shape of a sessile drop.

SUMMARY

In one aspect, methods of determining the shape of a sessile drop are described herein which, in some cases, can provide one or more advantages compared to other methods. For example, some embodiments of a method described herein can provide shape parameter information where an optical path from the measurement instrument to the profile of the sessile drop is obstructed and/or where the sessile drop is very small, such as less than about 1 μm in diameter at the interface of the drop and the surface on which the drop is disposed.

A method described herein, in some embodiments, comprises measuring a first shape parameter of a sessile drop to obtain a first shape parameter value, measuring a second shape parameter of the drop to obtain a second shape parameter value, and using the first and second shape parameter values to calculate a third shape parameter value of a third shape parameter of the drop. In some embodiments, the first, second and third shape parameters of the drop are selected from the group consisting of drop height, drop radius of curvature, contact interface diameter, drop wetting contact angle, drop resonance frequency, drop optical interference pattern, drop contact angle hysteresis, drop advancing contact angle, and drop contact force. In some instances, the third shape parameter is drop wetting contact angle.

Moreover, in some cases, the first and/or second shape parameters are measured vertically. In some embodiments, the first and/or second shape parameters are measured optically. Further, in some embodiments, the first and/or second shape parameters are measured from a substantially static angle. In addition, in certain cases, the first and/or second shape parameters are not measured by visual inspection of the drop. In some embodiments, the first and/or second shape parameters are measured by at least two of vertical measurement, optical measurement, measurement from a substantially static angle, and measurement without visual inspection of the drop.

In another aspect, methods of measuring the wettability of a surface are described herein. A method of measuring the wettability of a surface, in some embodiments, comprises disposing a sessile drop on the surface, measuring a first shape parameter of the drop to obtain a first shape parameter value, measuring a second shape parameter of the drop to obtain a second shape parameter value, and using the first and second shape parameter values to calculate a wetting contact angle of the drop on the surface. In some embodiments, the first and/or second shape parameters of the drop are selected from the group consisting of drop height, drop radius of curvature, contact interface diameter, drop wetting contact angle, drop resonance frequency, drop optical interference pattern, drop contact angle hysteresis, drop advancing contact angle, and drop contact force.

In a further aspect, additional methods of determining the shape of a sessile drop are described herein. A method of determining the shape of a sessile drop, in some embodiments, comprises measuring one or more first shape parameters to determine a geometric model of the drop, measuring one or more second shape parameter values of the drop to obtain one or more second shape parameter values, and using the one or more second shape parameter values to calculate one or more third shape parameter values of one or more third shape parameters. In some embodiments, the first, second and third shape parameters include all of the shape parameters of the geometric model. Further, in some cases, measuring the one or more second shape parameters comprises measuring the minimum number of second shape parameters necessary to calculate the one or more third shape parameters. In some embodiments, the geometric model is a spherical model or an oblate spheroid model.

Moreover, in some cases, the first and/or second shape parameters are measured vertically. In some embodiments, the first and/or second shape parameters are measured optically. Further, in some embodiments, the first and/or second shape parameters are measured from a substantially static angle. In addition, in certain cases, the first and/or second shape parameters are not measured by visual inspection of the drop. In some embodiments, the first and/or second shape parameters are measured by at least two of vertical measurement, optical measurement, measurement from a substantially static angle, and measurement without visual inspection of the drop. In some instances, the first, second and third shape parameters of the drop are selected from the group consisting of drop height, drop radius of curvature, contact interface diameter, drop wetting contact angle, drop resonance frequency, drop optical interference pattern, drop contact angle hysteresis, drop advancing contact angle, and drop contact force.

These and other embodiments are described further in the detailed description which follows.

DETAILED DESCRIPTION

Figure 1:
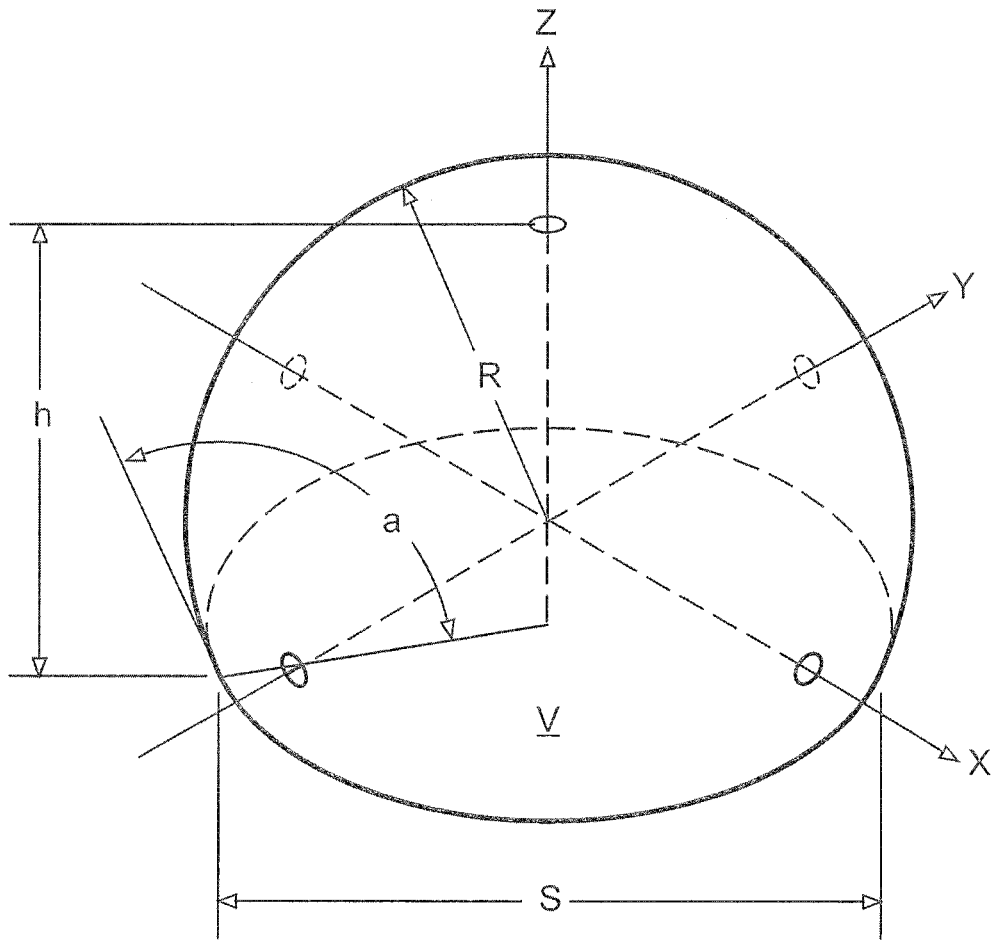
FIG. 1 illustrates a spherical geometric model of a sessile drop.

Embodiments described herein can be understood more readily by reference to the following detailed description, examples and drawings. Elements, apparatus and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

I. Methods of Determining the Shape of a Sessile Drop

In one aspect, methods of determining the shape of a sessile drop are described herein. In some embodiments, such a method can be carried out by measuring a first shape parameter of the drop to obtain a first shape parameter value, measuring a second shape parameter of the drop to obtain a second shape parameter value, and using the first and second shape parameter values to calculate a third shape parameter value of a third shape parameter of the drop.

The sessile drop of a method described herein can comprise, consist, or consist essentially of any material not inconsistent with the objectives of the present invention. For example, a drop can comprise, consist, or consist essentially of water, glycerine, a metal or a mixture or alloy of metals, a semiconductor material or a combination thereof. A metal or alloy, in some embodiments, comprises one or more of Cu, Ag, Au, Ga, In, Ge, Sn and Pb. A sessile drop of a method described herein, for example, can be formed of a metal or alloy employed in semiconductor manufacturing, such as metal or alloys used for electrical contacts.

Alternatively, a sessile drop can be formed of a semiconductor material. Suitable semiconductor materials can include II/VI semiconductors, III/V semiconductors, Group IV elemental semiconductor, or IV/VI semiconductors. In other cases, a semiconductor material comprises ternary or quaternary systems including materials, such as copper indium gallium selenide (CIGS). Non-limiting examples of II/VI semiconductors suitable for use in some embodiments described herein include binary semiconductors such as ZnS, ZnSe, ZnTe, CdS, CdSe, CdTe, HgS, HgSe, and HgTe or ternary semiconductors such as CdZnTe, HgCdTe, HgZnTe, and HgZnSe. Similarly, non-limiting examples of III/V semiconductors can include binary semiconductors such as GaN, GaP, GaAs, GaSb, InN, InP, InAs, and InSb or ternary or quaternary semiconductors such as InGaAs, InGaP, and InGaN. In some cases, a Group IV semiconductor comprises crystalline silicon, amorphous silicon, or germanium. Non-limiting examples of IV/VI semiconductors include PbS and PbSe. Further, a sessile drop described herein can be a fluid drop or a solid drop. A solid drop, in some cases, is a drop that has solidified on a surface after deposition of the drop in a fluid state.

Moreover, a sessile drop of a method described herein can have any size not inconsistent with the objectives of the present invention. In some cases, for example, a sessile drop has a diameter of up to about 5 mm, up to about 3 mm or up to about 1 mm at the interface of the drop with a surface on which the drop is disposed. In other instances, a sessile drop has an interfacial diameter of less than about 1 mm, less than about 500 µm, less than about 100 µm less than about 50 µm, less than about 20 µm, less than about 10 µm, or less than about 1 µm. In some embodiments, a sessile drop has an interfacial diameter between about 500 nm and about 1 mm, between about 1 µm and about 1 mm, between about 1 µm and about 0.5 mm, between about 1 µm and about 20 µm, between about 20 µm and about 500 µm, or between about 50 µm and about 200 µm.

In addition, the measured and/or calculated shape parameters of a method described herein can comprise any shape parameters not inconsistent with the objectives of the present invention. Further, a "shape parameter" can comprise any physical characteristic of a drop that provides information regarding the shape of the drop. Moreover, a shape parameter can be consistent with a geometric model of a drop, including a theoretically or empirically derived geometric model. An example of such a geometric model is illustrated in FIG. 1. The geometric model of FIG. 1 defines various shape parameters relative to a Cartesian (x, y, z) coordinate system. However, other coordinate systems, such as a polar coordinate system, could also be used. Example shape parameters illustrated by FIG. 1 include: drop height (h), drop radius of curvature (R), the diameter of the interface between the drop and a substrate surface (the "contact interface diameter" or "interfacial diameter) (s), and drop wetting contact angle ($\alpha$). In addition, in some cases, drop volume (V) could also be used as a shape parameter. In other instances, drop volume is not used as a shape parameter. In particular, utilization of drop volume as a shape parameter, in some embodiments, can be undesirable in certain circumstances. For example, in instances wherein a liquid sessile drop comprises a small drop volume, evaporation of the liquid drop may result in error or loss of precision in a calculation based on drop volume as a shape parameter. Further, in some cases, drop volume may be unknown or difficult to measure based on environmental or experimental conditions. Thus, in some embodiments, a method described herein can be used to determine the shape of a sessile drop without the need to measure or otherwise determine the volume of the drop.

While FIG. 1 illustrates certain shape parameters, one of skill in the art would recognize that additional shape parameters can also be described by a geometric model of a drop. Further, as described further hereinbelow, a shape parameter can also comprise drop resonance frequency, drop optical interference pattern (as by back scattering and/or by reflective modes), drop contact angle hysteresis, drop advancing contact angle, and drop contact force. Moreover, while FIG. 1 illustrates an example geometric model describing a spherical drop, it is to be understood that additional geometric models can also be used. For example, in some cases, an oblate spheroid geometric model can be used to describe the drop.

As described herein, directly measuring one or more of the foregoing shape parameters can permit one or more additional shape parameters to be calculated, rather than being directly measured. In particular, in some embodiments, directly measuring two of the foregoing shape parameters can permit a third shape parameter to be calculated using the measured values of the first and second shape parameters. In certain other embodiments, directly measuring three of the foregoing shape parameters can permit a fourth shape parameter to be calculated using the measured values of the first, second and third shape parameters. Thus, a method described herein can permit the accurate determination of shape parameters that may be difficult to measure directly in a specific situation.

In general, any combination of first and second shape parameters not inconsistent with the objectives of the present invention can be used to calculate a third shape parameter. In some cases, the first and second shape parameters of a method described herein are selected based on a relationship between the shape parameters consistent with a geometric model of the drop, such that the first and second shape parameters provide additional information regarding the shape of the drop. For example, in some embodiments, the first shape parameter is drop radius of curvature and the second shape parameter is drop height. In some such embodiments, the third shape parameter can be the drop wetting contact angle. In other cases, the first shape parameter is drop resonance frequency and the second shape parameter is drop optical interference. In still other instances, the first shape parameter is drop radius of curvature and the second shape parameter is drop resonance frequency.

Further, in some embodiments, the third shape parameter of a method described herein can be selected based on the first and second shape parameters. In certain other cases, the third shape parameter can be selected prior to measurement of the first and second shape parameters, and the first and second shape parameters can be selected based on the preselected third shape parameter.

Moreover, in some embodiments, a specific geometric model of a drop can be obtained, identified, or determined by first measuring one or more first shape parameters of the drop. Additional shape parameters can then be selected for subsequent measurement based on the geometric model obtained, identified, or determined by the measurement of the one or more first shape parameters. For example, in some instances, measuring the one or more first shape parameters can determine that the shape of the drop is generally spherical or of an oblate spheroid shape. Then, in some embodiments, further determination and measurement of the shape of the drop can be based on a geometric model corresponding to the general shape of the drop obtained, identified, or determined by measuring the one or more first shape parameters. Further, in some cases, measuring one or more second shape parameters comprises measuring the minimum number of second shape parameters necessary to calculate one or more third shape parameter values, including based on the identified geometric model of the drop. In some such instances, the one or more second shape parameters can then be used to calculate one or more third shape parameter values. Additionally, in certain embodiments, the first, second and third shape parameters comprise all of the shape parameters of the sessile drop.

Measured shape parameters, such as first and second shape parameters, can be measured in any manner not inconsistent with the objectives of the present invention. For example, in some embodiments, the first and/or second shape parameter is measured vertically or from above, as opposed to laterally or from the side. In some cases, a shape parameter that is measured "vertically" or in a "top-down" manner is measured from an orientation or configuration that is substantially perpendicular to the substrate surface on which the drop is disposed. Thus, measurement occurring vertically stands in contrast to "horizontal" or "lateral" measurement techniques or devices oriented or aligned in a plane parallel to the substrate surface or configured to measure a shape parameter of the drop from a side portion or profile of the drop. As described herein, vertical measurement of a shape parameter, in some cases, can permit the accurate determination of the shape of a drop that cannot be readily observed from the side, such as may occur when a drop is disposed on a surface having side walls or other obstructions to a lateral line of sight to the interface between the drop and the surface. Some vertical measurement techniques suitable for use in some embodiments described herein are described in more detail in the specific Examples below.

Moreover, in some embodiments, a first and/or second shape parameter is measured optically. In some cases, a shape parameter measured "optically" is measured using a device and/or technique that probes a sample using electromagnetic radiation and/or obtains information about a sample by detecting electromagnetic radiation. For example, in some embodiments, a first and/or second shape parameter is measured using optical microscopy.

Further, in some embodiments, measurement of a first and/or second shape parameter occurs from a substantially static angle. A "substantially" static angle, in some cases, varies by less than about 15 degrees, less than about 10 degrees, less than about 5 degrees, or less than about 1 degree during the course of the measurement. Methods or devices measuring a shape parameter, such as drop radius of curvature or drop height, from a substantially static angle stand in contrast to methods or devices which utilize transversal of a range of angles to measure a shape parameter.

Additionally, a shape parameter of a drop described herein, in some cases, can be measured without visual inspection of the drop, where "visual inspection" refers to the calculation of a shape parameter, such as drop wetting contact angle, based on the visual inspection of a visual representation of the drop. For example, in some cases, visual inspection comprises photographing a sessile drop and using the photograph of the drop to measure the wetting contact angle, where such measurement can be carried out manually using a tool such as a protractor or electronically using electronic hardware and/or software.

In some embodiments, a method or device for measuring a first and/or second shape parameter can incorporate at least two of vertical measurement, optical measurement, measurement from a substantially static angle, and/or measurement without visual inspection. Methods or devices for measurement of a first and/or second shape parameter consistent with the foregoing can include, without limitation, one or more of the following: measurement of drop dynamics, such as resonance frequency; excitation, such as by oscillation, of the drop to determine drop dynamics; confocal microscopy, such as by use of a confocal microscope; measurement utilizing an optical lever; and observation of optical interference patterns of the drop. In some embodiments, a single method or device can be utilized to measure both a first and a second shape parameter. In certain other embodiments, a first method or device can be used to measure a first shape parameter, and a second method or device can be used to measure a second shape parameter.

Methods or devices for measurement of first and/or second shape parameters, in some cases, can be selected based on appropriateness of the method or device for measuring the shape parameter. In other cases, methods or devices for measurement of first and/or second shape parameters can be selected based on limitations of the substrate surface or the drop itself. For example, circumstances can arise which prevent an unobstructed lateral line of sight, or wherein drop size renders certain measurement methods or devices functionally inoperable.

Figure 2A:
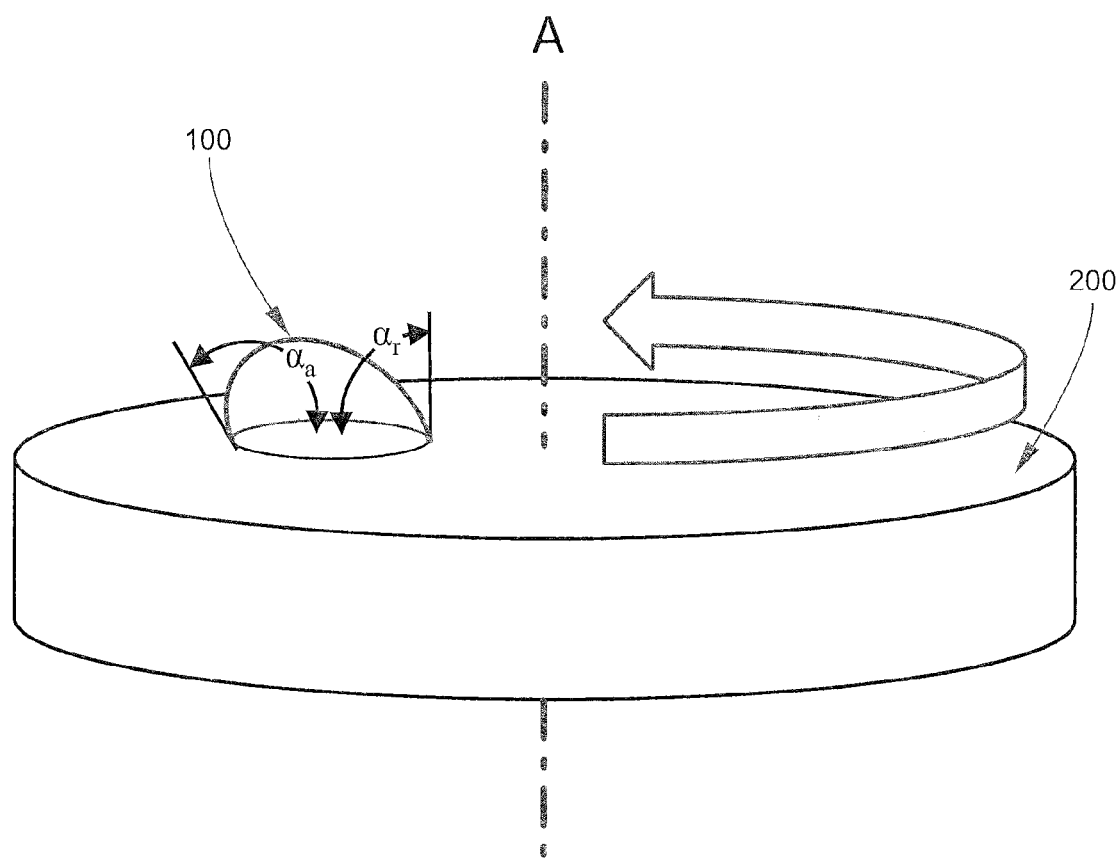
FIGS. 2A and 2B illustrate devices that can be used to carry out a method according to some embodiments described herein.
Figure 2B:
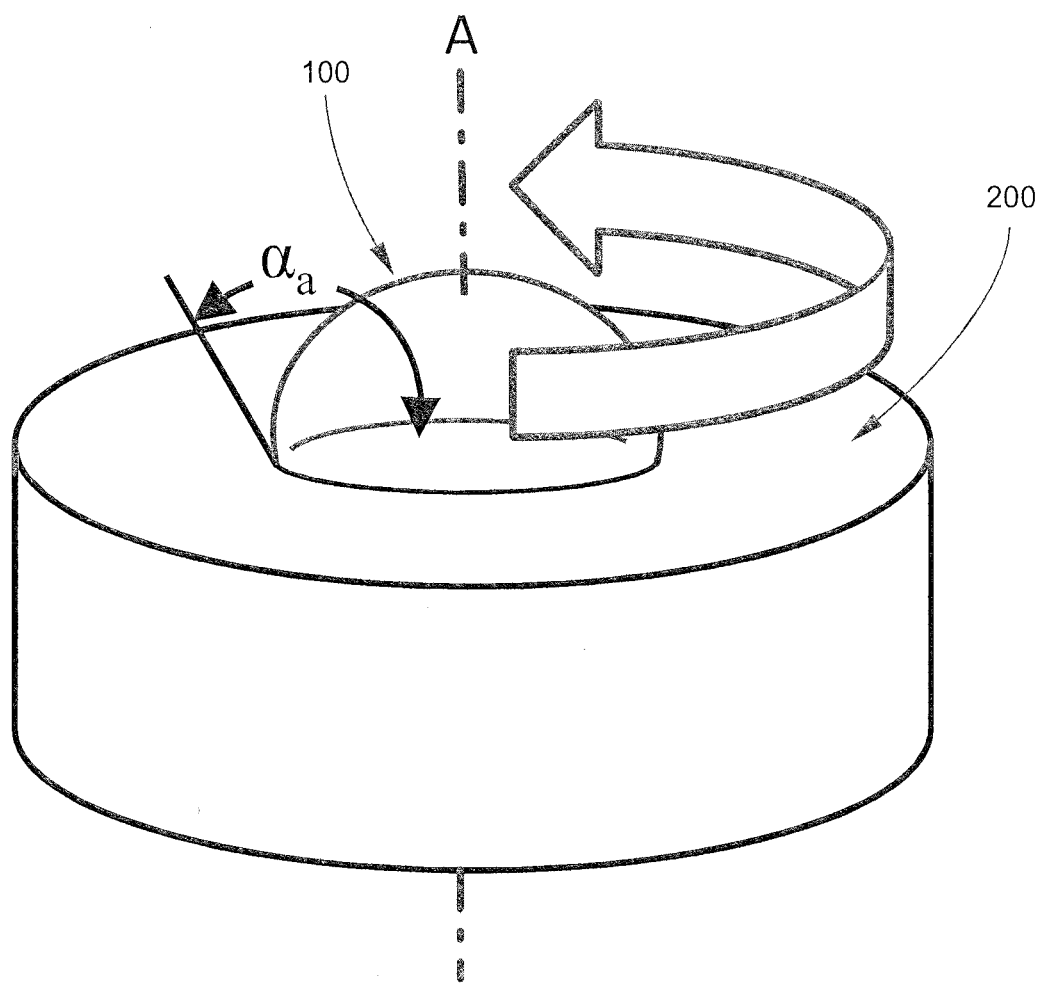

In some embodiments, however, a lateral line of sight is available. In some such instances, a first and/or second shape parameter can be measured either vertically or a horizontally. Horizontal measurements of a first and/or second shape parameter can be carried out in any manner not inconsistent with the objectives of the present invention. In some cases, for example, a horizontal measurement of a shape parameter can be carried out by contact angle hysteresis (on-axis and/or off-axis) and/or contact force measurement. One embodiment of an experimental setup that can be used to measure off-axis contact angle hysteresis is illustrated in FIG. 2A. In the embodiment of FIG. 2A, a sessile drop (100) is disposed on a surface (200), and the surface (200) is rotated about an axis (A). The drop (100) is disposed in the lateral direction away from the axis (A). One embodiment of an experimental setup that can be used to measure on-axis contact angle hysteresis is illustrated in FIG. 2B. In the embodiment of FIG. 2B, the setup of FIG. 2A is modified by placement of the drop (100) such that the axis (A) is collinear with the center of the drop (100). In both setups, the change in contact angle can be determined as a shape parameter. More specifically, the setups of FIGS. 2A and 2B each permit the measurement of an advancing contact angle ($\alpha_a$) of the drop associated with a centrifugal force resulting from rotation of the surface (200) in the direction identified by the arrows in FIGS. 2A and 2B. In addition, in the embodiment of FIG. 2A, it is also possible to determine the receding contact angle ($\alpha_r$). Both the advancing contact angle ($\alpha_a$) and the receding contact angle ($\alpha_r$) can be measured by a lateral line of site method, including a method comprising the generation of a visual representation of the drop.

Figure 3:
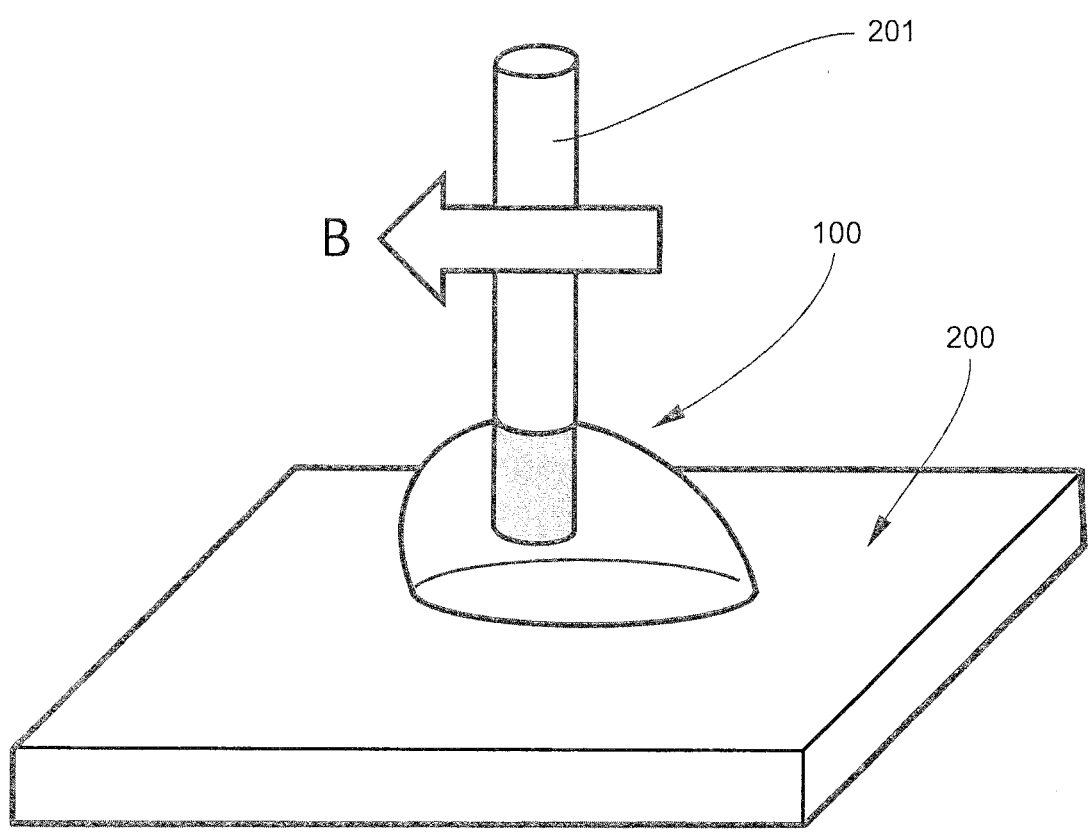
FIG. 3 illustrates a device that can be used to carry out a method according to one embodiment described herein.

FIG. 3 illustrates another shape parameter measurement that can be used in some embodiments described herein. As illustrated in FIG. 3, a sessile drop (100) is disposed on a surface (200), and a force applicator (210) is used to apply a directional force to the drop (100) as indicated by the arrow (C). In this manner, the resistance of the drop to change in shape and/or contact parameters can be measured. Additional methods of measuring first and/or second shape parameters are further described in the specific examples below.

Following measurement of the first and second shape parameters, a method described herein further comprises calculating a third shape parameter value from the values of the first and second shape parameters. The third shape parameter value can be calculated in any manner not inconsistent with the objectives of the present invention. In some embodiments, the third shape parameter value is calculated based on a relationship derived from a geometric model of the drop. For example, in some cases, the first shape parameter is the drop height, the second shape parameter is the drop radius of curvature, and the third shape parameter value is a wetting contact angle calculated according to Equation (1):

$$\alpha = \cos^{-1}\left(1 - \frac{h}{R}\right), \qquad (1)$$

wherein $\alpha$ is wetting contact angle, h is drop height, and R is drop radius of curvature. A third shape parameter value may also be calculated using other relationships and/or formulas, as described further hereinbelow.

II. Methods of Measuring the Wettability of a Surface

In another aspect, methods of measuring the wettability of a surface are described herein. In some embodiments, a method of measuring the wettability of a surface comprises disposing a sessile drop on the surface, measuring a first shape parameter of the drop to obtain a first shape parameter value, measuring a second shape parameter of the drop to obtain a second shape parameter value, and using the first and second shape parameter values to calculate a wetting contact angle of the drop on the surface. In some such cases, the wettability of the surface is described in terms of the wetting contact angle of the drop on the surface.

Any sessile drop not inconsistent with the objectives of the present invention may be used to measure the wettability of a surface according to a method described herein. In some cases, the sessile drop comprises a sessile drop described hereinabove in Section I. For example, in some embodiments, a drop comprises water, glycerine, a metal or a mixture or alloy of metals, a semiconductor material, or a combination thereof.

Further, any shape parameters not inconsistent with the objectives of the present invention may be used as a first and/or second shape parameter of a method described herein. In some cases, a first and/or second shape parameter comprises a shape parameter described hereinabove in Section I. For example, in some instances, the first and/or second shape parameter is selected from the group consisting of drop height, drop radius of curvature, contact interface diameter, drop wetting contact angle, drop resonance frequency, drop optical interference pattern, drop contact angle hysteresis, drop advancing contact angle, and drop contact force.

Similarly, the first and/or second shape parameters can be measured in any manner not inconsistent with the objectives of the present invention. In some cases, the first and/or second shape parameter is measured in a manner described hereinabove in Section I or hereinbelow in the specific examples. In some embodiments, the first and/or second shape parameter is measured vertically, optically, at a substantially static angle, and/or without visual inspection of the drop.

Additionally, calculating the wetting contact angle using the first and second shape parameter values can be carried out in any manner not inconsistent with the objectives of the present invention, including in a manner described hereinabove in Section. In some cases, for instance, the wetting contact angle is calculated according to Equation (1) hereinabove.

Some embodiments described herein are further illustrated in the following non-limiting examples.

EXAMPLE 1

Method of Determining the Shape of a Sessile Drop

Figure 4:
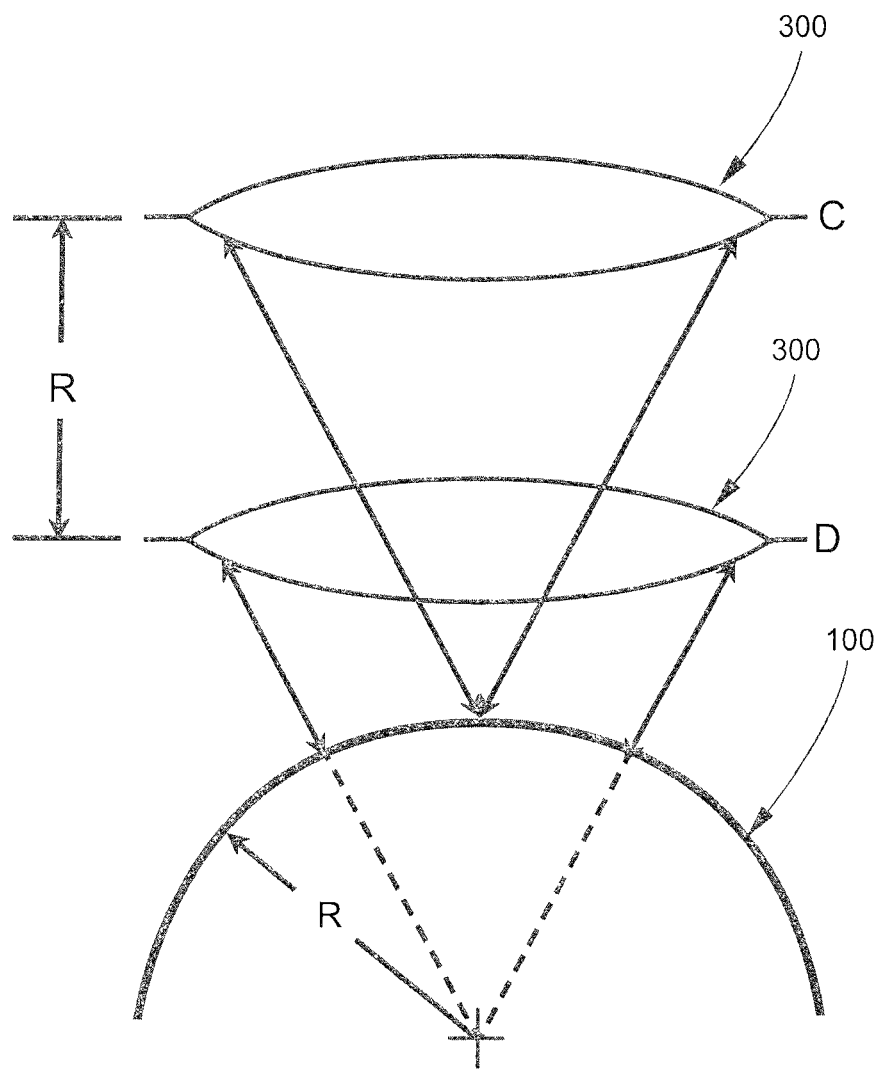
FIG. 4 illustrates schematically a method of measuring a shape parameter according to one embodiment described herein.

A method of determining the shape of a drop according to one embodiment described herein was carried out as follows. For the following example, drop radius of curvature and drop height were selected as first and second shape parameters, respectively. Radius of curvature was determined by means of a radius bench technique consistent with Weise et al., "Imaging of spheres with the confocal scanning optical microscope," *Optics letters* 21.22 (1996), 1800-1802. FIG. 4 illustrates a schematic depiction of the relationship between radius of curvature and translation of the objective (300) of a confocal microscope during measurement of a sessile drop (100) by radius bench confocal microscopy. As illustrated in FIG. 4, the objective (300) is used to measure an apex position of the drop (100), establishing a first position (C). The objective is then vertically translated towards the substrate surface until an imaginary image appears. The imaginary image corresponds to the center of the radius of curvature of the drop (100). The center of the radius of curvature establishes a second objective position (D). The distance of translation of the objective from the first position (C) to the second objective position (D) corresponds to the radius of curvature of the drop.

Figure 5:
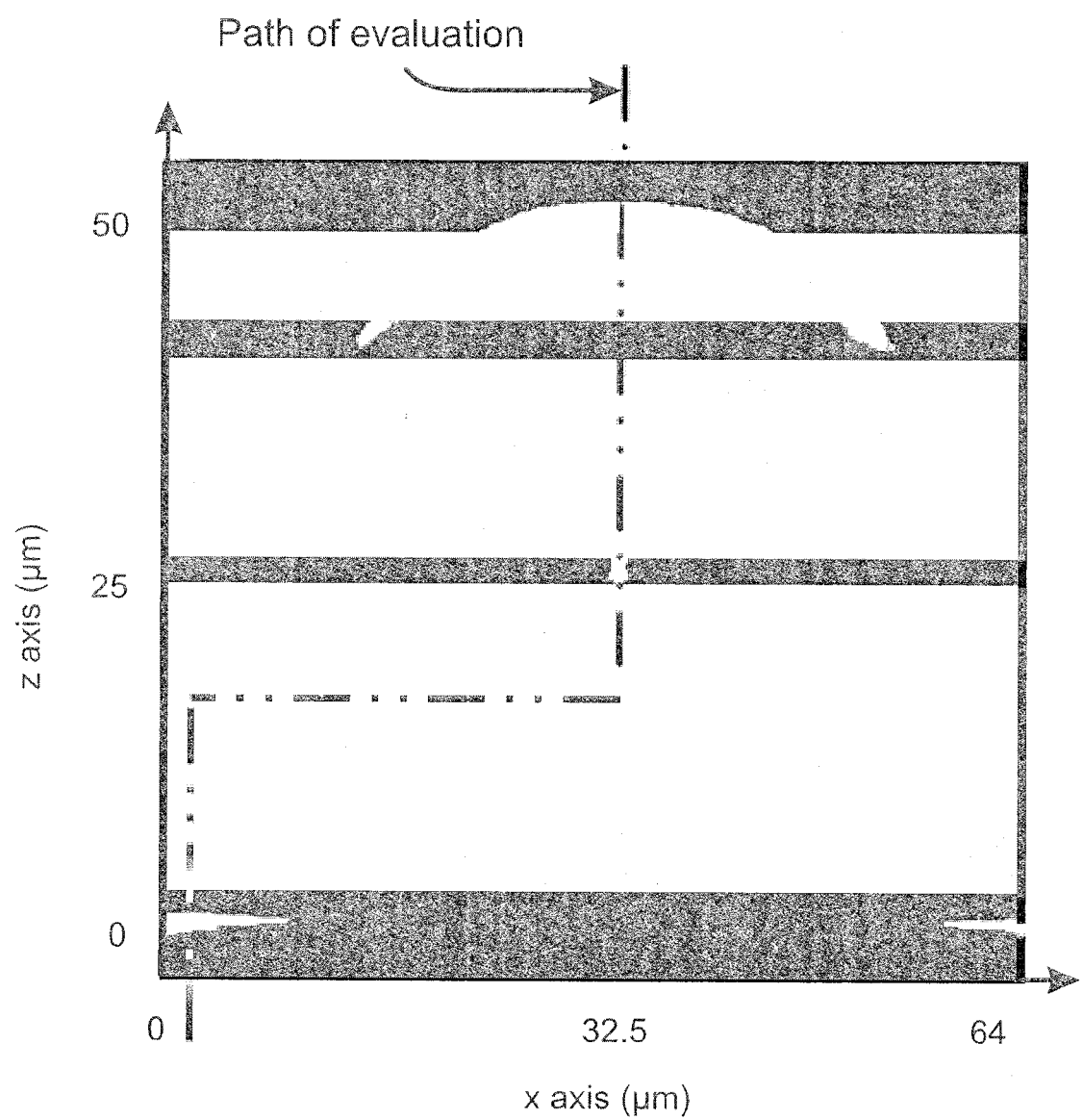
FIG. 5 illustrates data obtained by a method according to one embodiment described herein.
Figure 6:
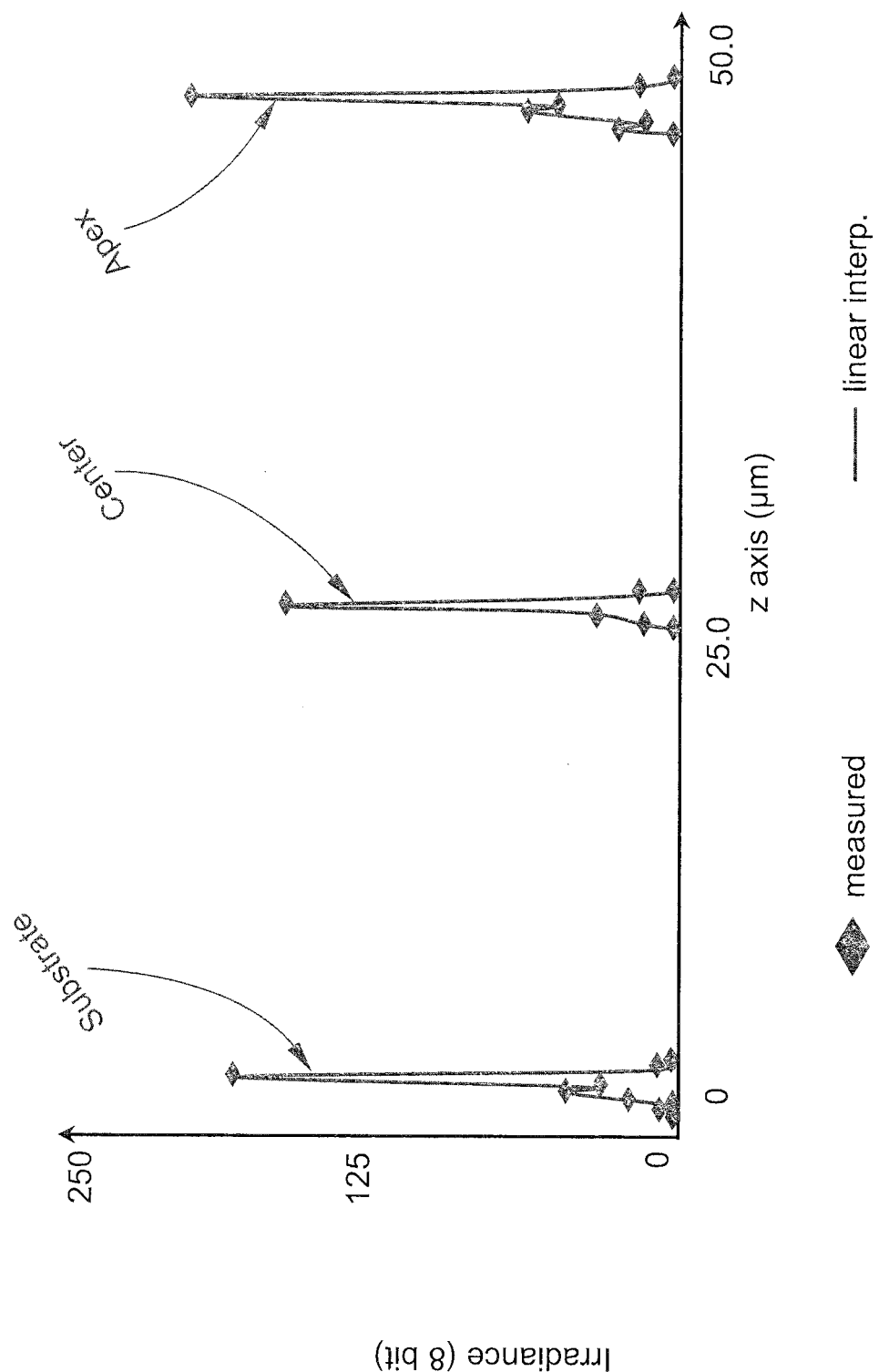
FIG. 6 illustrates data obtained by a method according to one embodiment described herein.

Using a radius bench confocal microscopy technique, a confocal microscope image of a silica sphere (diameter=53 μm) resting on a silica substrate was produced using a commercial scanning confocal microscope (Olympus LEXT OLS 4000). Although this example utilized a silica sphere to represent a sessile drop, it is to be understood that any drop consistent with the objectives of the present invention, such as a liquid sessile drop, could be analyzed in the same manner. The confocal scan was configured with height increments of 250 nm, over a range spanning 5 μm above the sphere apex to 5 μm below the substrate surface. The confocal microscopy scan provided a series of 2D matrices of irradiance values. To reduce the number of measured planes, the scan only included regions of interest (three scans each including the sphere apex, the center peak, and the substrate surface). Each confocal plane was then stacked vertically in an array, resulting in a 4D dataset (x, y, z, and irradiance), where the vertical voxel column associated with the axis of symmetry of the drop was evaluated by plotting the irradiance as a function of displacement in the z axis. The resulting data is illustrated in FIG. 5 as a vertical confocal slice of the 4D dataset, with gray regions indicating non-measured regions. The dashed line in FIG. 5 illustrates the path of evaluation along which the irradiance was used for feature measurement. A plot of the irradiance along the path of evaluation is illustrated in FIG. 6.

From this measurement, the distance from the highest measured irradiance on the substrate surface to the highest measured irradiance on the sphere's apex was 50.0 μm, with the location of the center maximum at a distance of 25.0 μm from both the top surface and the substrate. Alternative confocal microscopy methods can comprise moving the objective of the confocal microscope laterally a distance greater than the measured drop radius of curvature, and repeating the technique applied to the drop beginning at the height corresponding to the drop apex. Such methodology would result in a measurement of drop height.

Using these values as first and second shape parameter values, a third shape parameter was calculated. For Example 1, wetting contact angle was selected as the third shape parameter. Wetting contact angle was then calculated according Equation 1 above. In this case, h was 50 μm, and R was 25 μm. The resultant calculated contact angle was therefore 180°, which is consistent with an expected wetting contact angle of a rigid sphere on a rigid substrate surface.

EXAMPLE 2

Method of Determining the Shape of a Sessile Drop

A method of determining the shape of a sessile drop according to one embodiment described herein is carried out as follows. The first shape parameter is the drop resonance frequency. The second shape parameter is the drop radius of curvature. A third shape parameter is calculated using the drop resonance frequency and drop radius of curvature.

Not intending to be bound by theory, it is believed that a liquid drop assumes the shape of a spherical cap due to the associated surface energies of each interface of the drop. It is believed that the energies in the system will equilibrate to a state wherein the sum of the interfacial energies is at a minimum. This equilibrium point is known as the Gibbs energy minimum. If a kinetic disturbance is introduced into a wetting system, the resulting Gibbs energy minimum will shift, resulting in a system oscillation. Again not intending to be bound by theory, it is believed that the oscillation frequency is a function of the system parameters and, if measured on a drop having a known density, surface tension and viscosity, can be used as a shape parameter in the definition of the shape of the sessile drop.

Figure 7A:
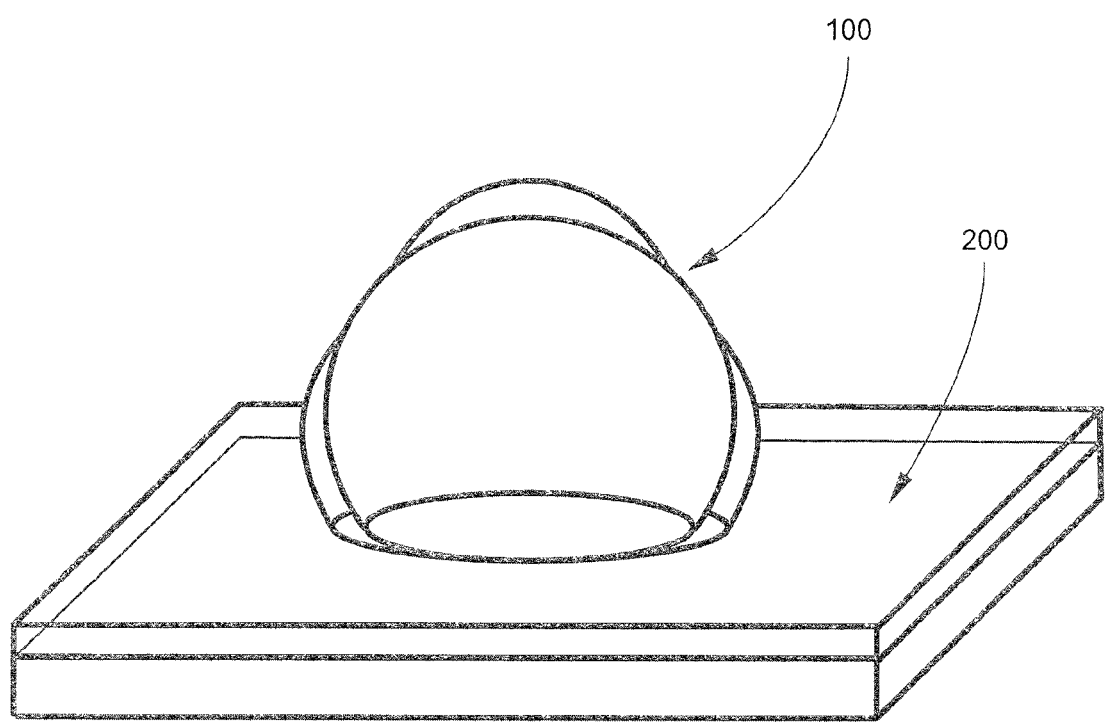
FIGS. 7A, 7B, 7C, and 7D illustrate devices that can be used to carry out a method according to some embodiments described herein.
Figure 7B:
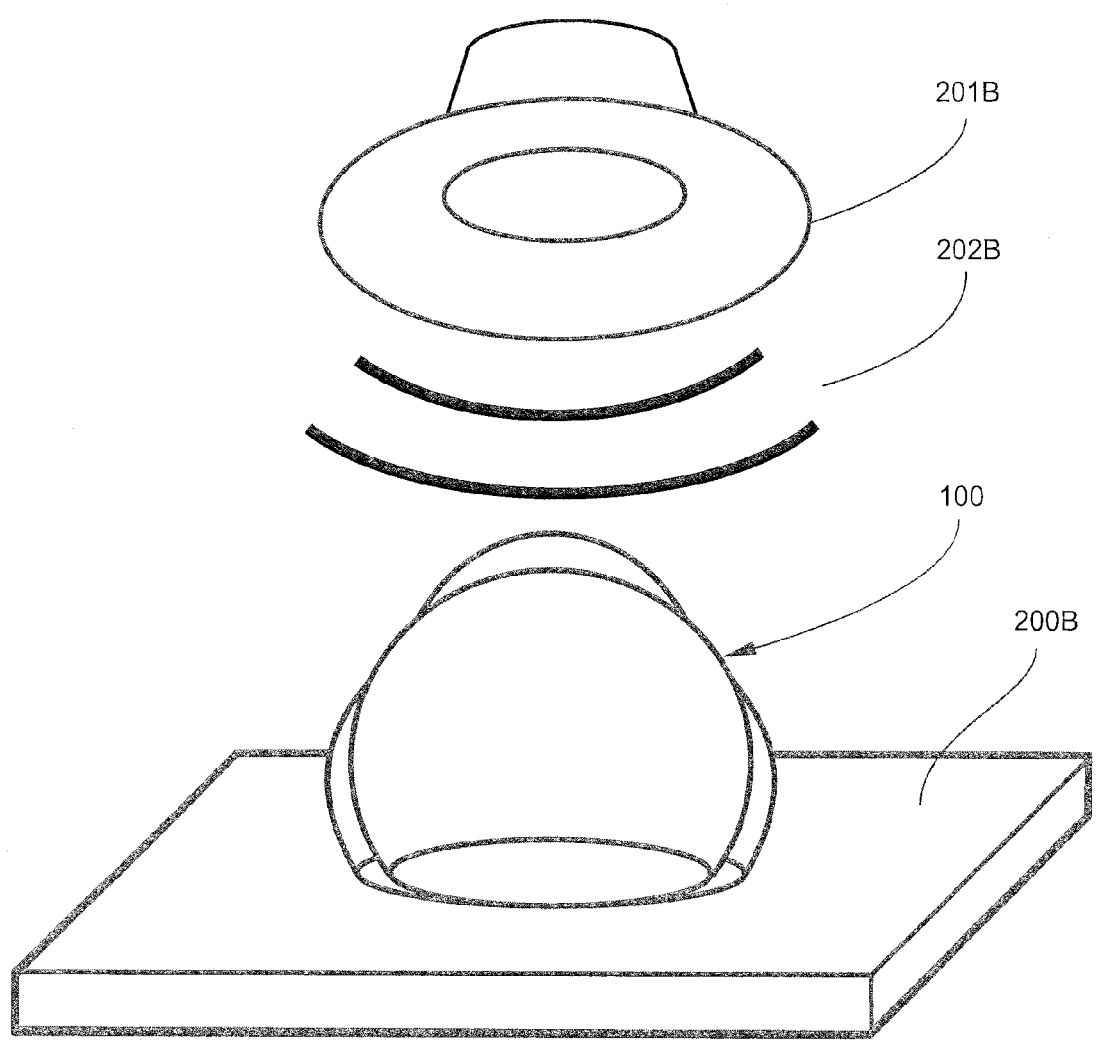
Figure 7C:
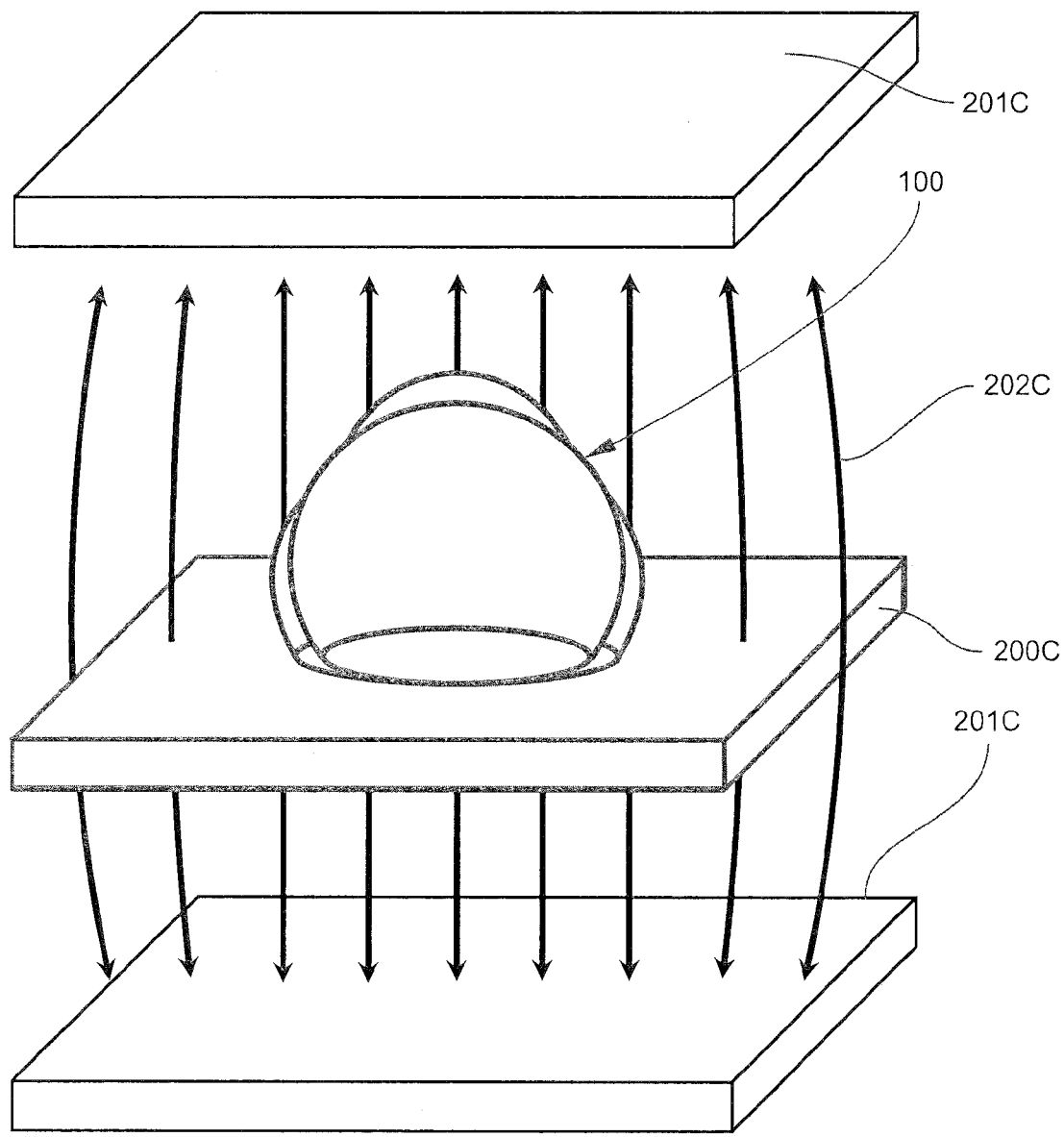
Figure 7D:
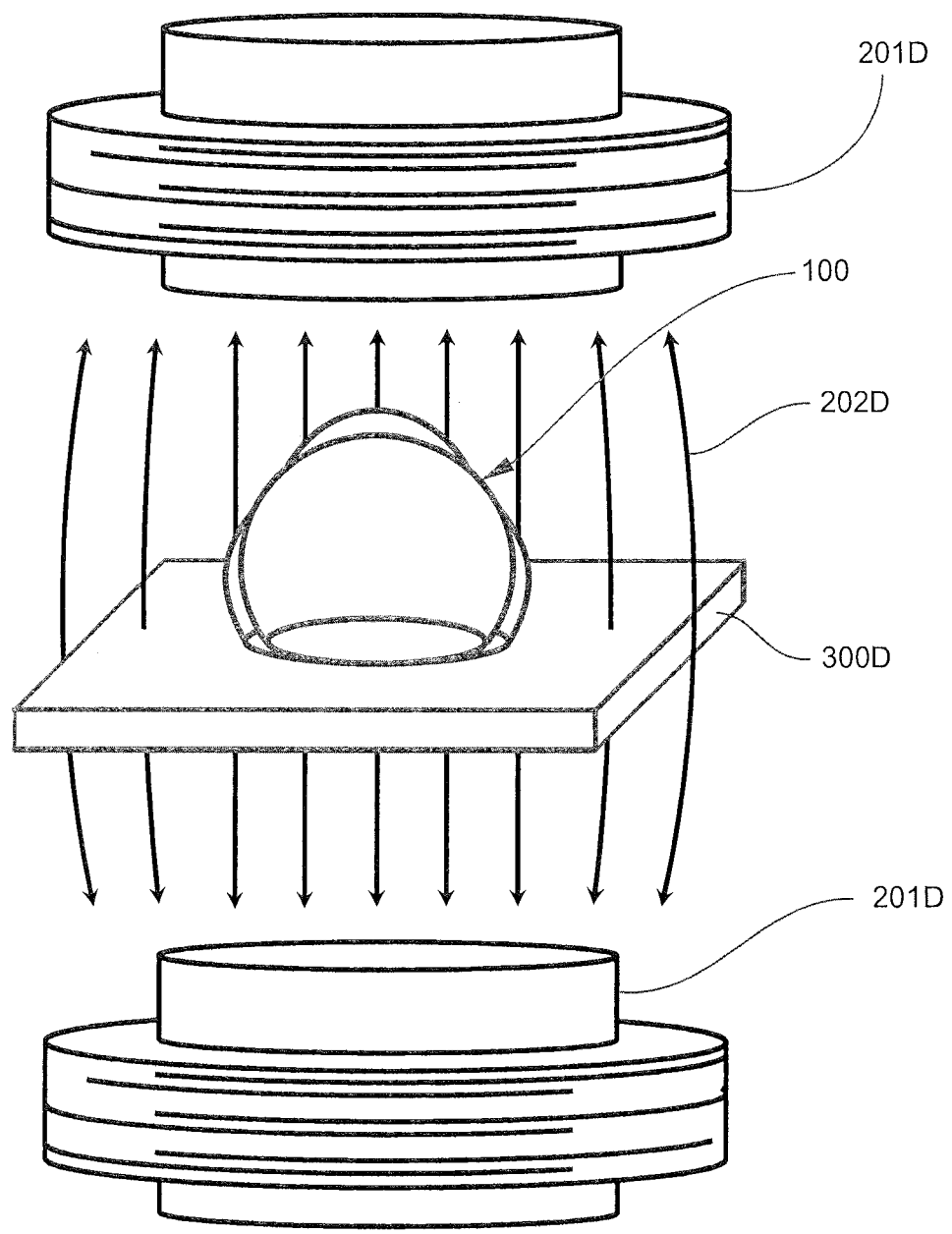

As illustrated in FIG. 7A, a sessile drop (100) can be excited by a piezoelectric actuator (200A) consistent with the methods described by James et al., "Vibration-induced drop atomization and bursting," *Journal of Fluid Mechanics* 476 (2003), 1-28. Other methods may also be used to initiate excitation of the drop to produce oscillation. For example, one alternative excitation method can include acoustic actuation, as illustrated in FIG. 7B. In FIG. 7B, a sessile drop (100) is disposed on a surface (200B), and an acoustic actuator (201B) emits an oscillating pressure wave (202B), which in turn actuates the drop into an oscillating state. Another example actuation method is excitation by application of an oscillating electric field or electrostatic excitation. FIG. 7C illustrates actuation by electric field, whereby a pair of electrodes (201C) provide the drop (100) with an alternating electric field (202C), increasing the surface energy and resulting in oscillation of the drop as the Gibbs energy minimum shifts. FIG. 7D illustrates a further excitation means, whereby a pair of electromagnets (201D) opposite the drop (100) apply an alternating magnetic field (202D), resulting in oscillation of the drop. Further, in some cases, a sessile drop can be excited by an oscillating gravitational field. One example of such excitation is placement of the drop on a spinning surface having a rotational axis substantially perpendicular to, or horizontal to, earth's gravitational field. Spinning of the drop can result in the drop oscillating as it is acted upon by changing gravitational pull.

Figure 8A:
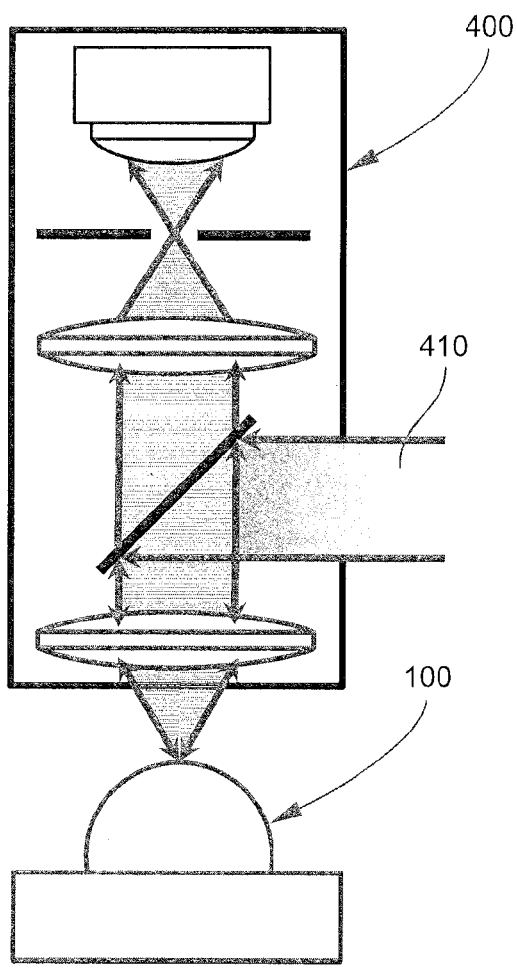
FIGS. 8A and 8B illustrate a device that can be used to carry out a method according to one embodiment described herein.
Figure 8B:
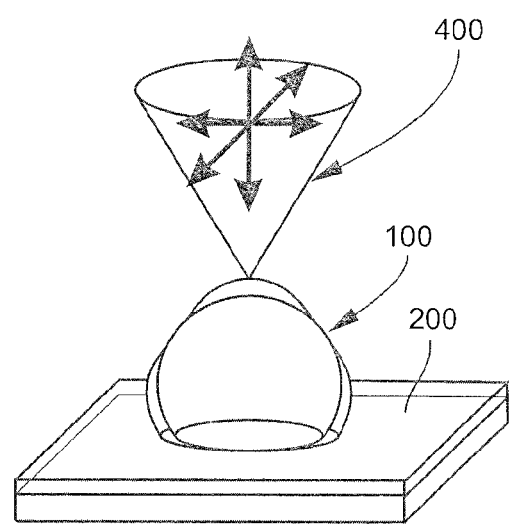

The dynamics of the oscillating drop can then be measured by a scanning confocal microscope. The resultant measurement provides measurements for both drop radius of curvature and drop oscillation dynamics such as the drop resonance frequency. The scanning confocal microscope technique can yield an output signal that is at exactly twice the oscillation frequency of the sessile drop oscillation and an amplitude proportional to the deviation in distance of the drop from the focal plane. FIGS. 8A schematically illustrates a confocal microscopy setup (400) utilizing monochromatic light (410), and FIG. 8B illustrates schematically how the setup (800) of FIG. 8A can coordinate with a piezoelectric plate (200) to oscillate the sessile drop (100) for contemporaneous measurement of the radius of curvature and dynamics of an oscillating sessile drop.

When fit to a geometric model of a drop as depicted in FIG. 1, the relationship between drop resonance frequency and drop radius of curvature can be used to calculate additional shape parameters consistent with the geometric model.

EXAMPLE 3

Method of Determining the Shape of a Sessile Drop

Figure 9:
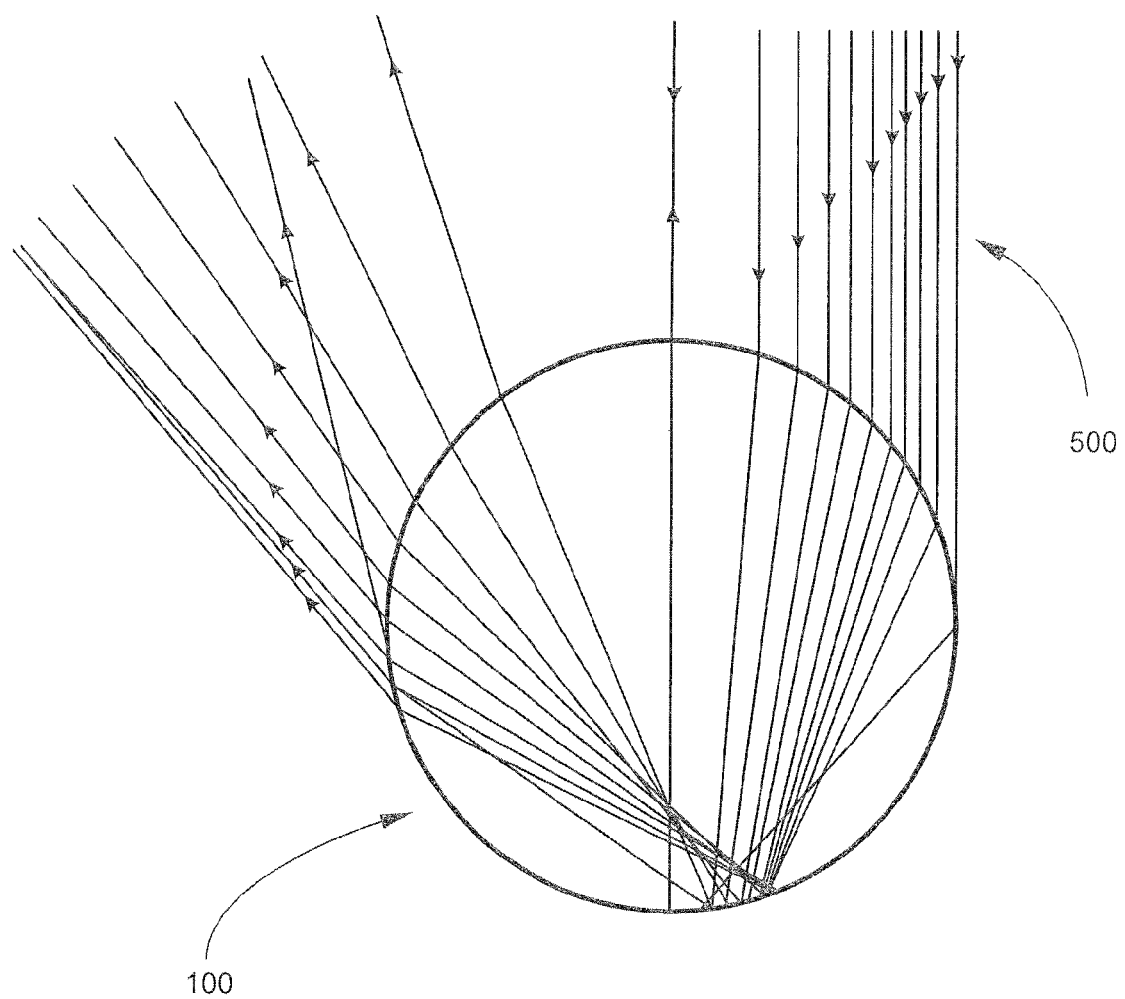
FIG. 9 illustrates schematically a step of a method of measuring a shape parameter according to one embodiment described herein.

A method determining the shape of a sessile drop according to one embodiment described herein is carried out as follows. At least one shape parameter of a sessile drop can be determined by measurement of interference patterns as by back scattering and/or reflective modes. Used in combination with a second shape parameter such as drop resonance frequency, a third shape parameter can be calculated. For example, forward scattering interference patterns can be used to produce an interference fringe pattern. The fringe period of the resultant pattern can be used to determine one or more shape parameters, such as diameter of the drop. FIG. 9 illustrates a planar slice ray tracing of incident light (500) on a sessile drop (100) with a high wetting contact angle. It can be seen that the light exiting the sessile drop (100) can produce an interference or diffraction pattern with information that is related to the shape parameters of the sessile drop, including with reference to a geometric model of the drop.

Figure 10:
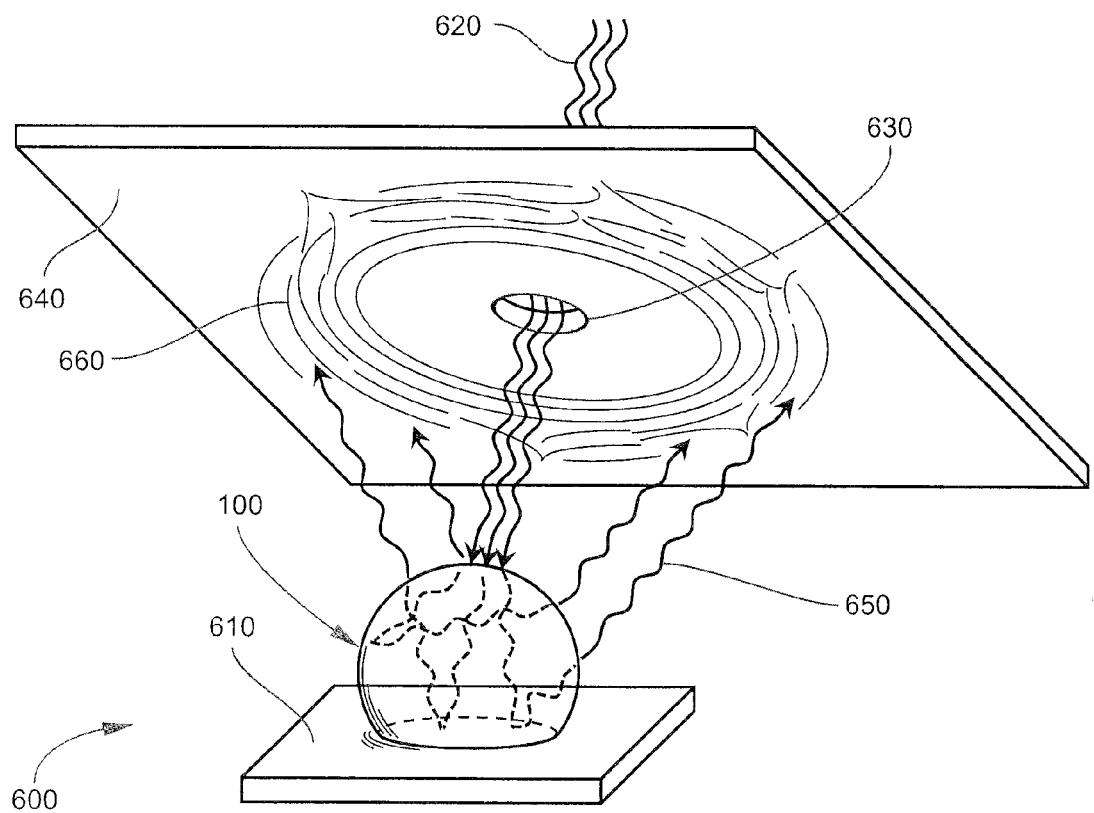
FIG. 10 illustrates a device that can be used to carry out a method according to one embodiment described herein.

An example measurement setup (600) utilizing forward scattering of light is illustrated in FIG. 10. In FIG. 10, measurement of at least one shape parameter of a sessile drop (100) resting on a substrate surface (610) can be performed by directing incident light (620) onto a surface of the drop (100) through an aperture (630) in a viewing screen (640). A portion of the incident light (620) is transmitted through the surface and another portion is reflected, indicated by the reflected light (650) arrows. As a result, some of the incident light (620) is transmitted through the drop (100), some incident light (620) is reflected by the substrate surface (610), some of the incident light (620) is reflected by the external surface of the drop (100), and some of the incident light (620) is reflected by the internal surface of the drop (100) and transmitted a second time through the drop. Reflected light appears on the viewing screen in a pattern (660) related to shape parameters of the drop.

Figure 11A:
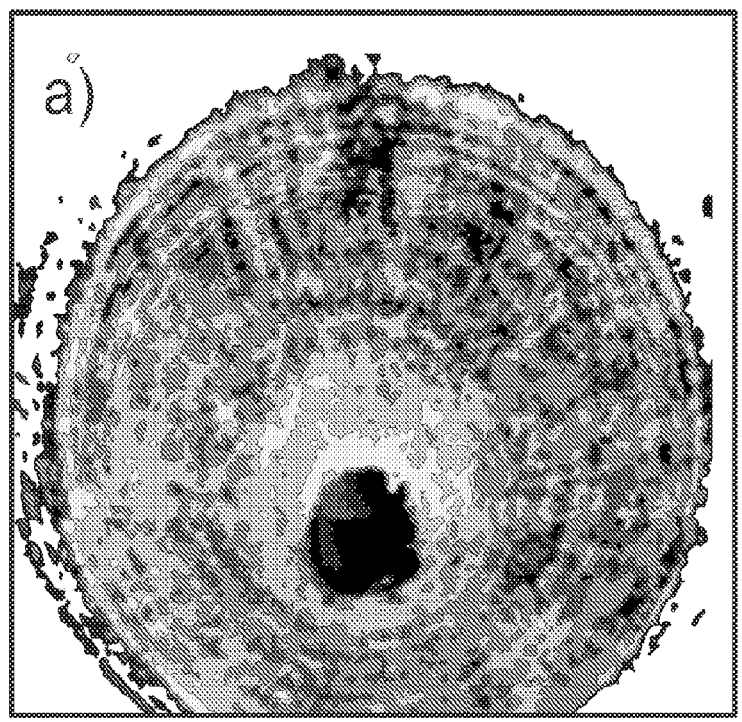
FIGS. 11A and 11B illustrate data obtained by a method according to one embodiment described herein.
Figure 11B:
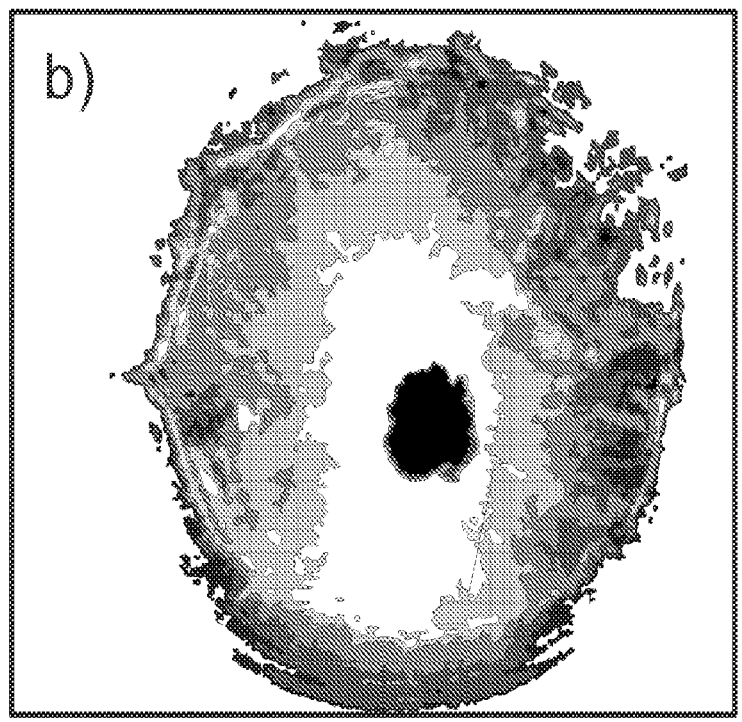

An example diffraction pattern from interference of internally reflected light and externally reflected light is illustrated in FIGS. 11A and 11B. FIG. 11A illustrates the resulting diffraction pattern from incident light on a 250µm diameter glass sphere on a planar surface. FIG. 11 B illustrates the diffraction pattern from incident light on the glass sphere with an index matched solution surrounding its base. Such interference patterns can be used to extract at least one shape parameter, such as the diameter, of the drop when fit to a geometric model.

Figure 12:
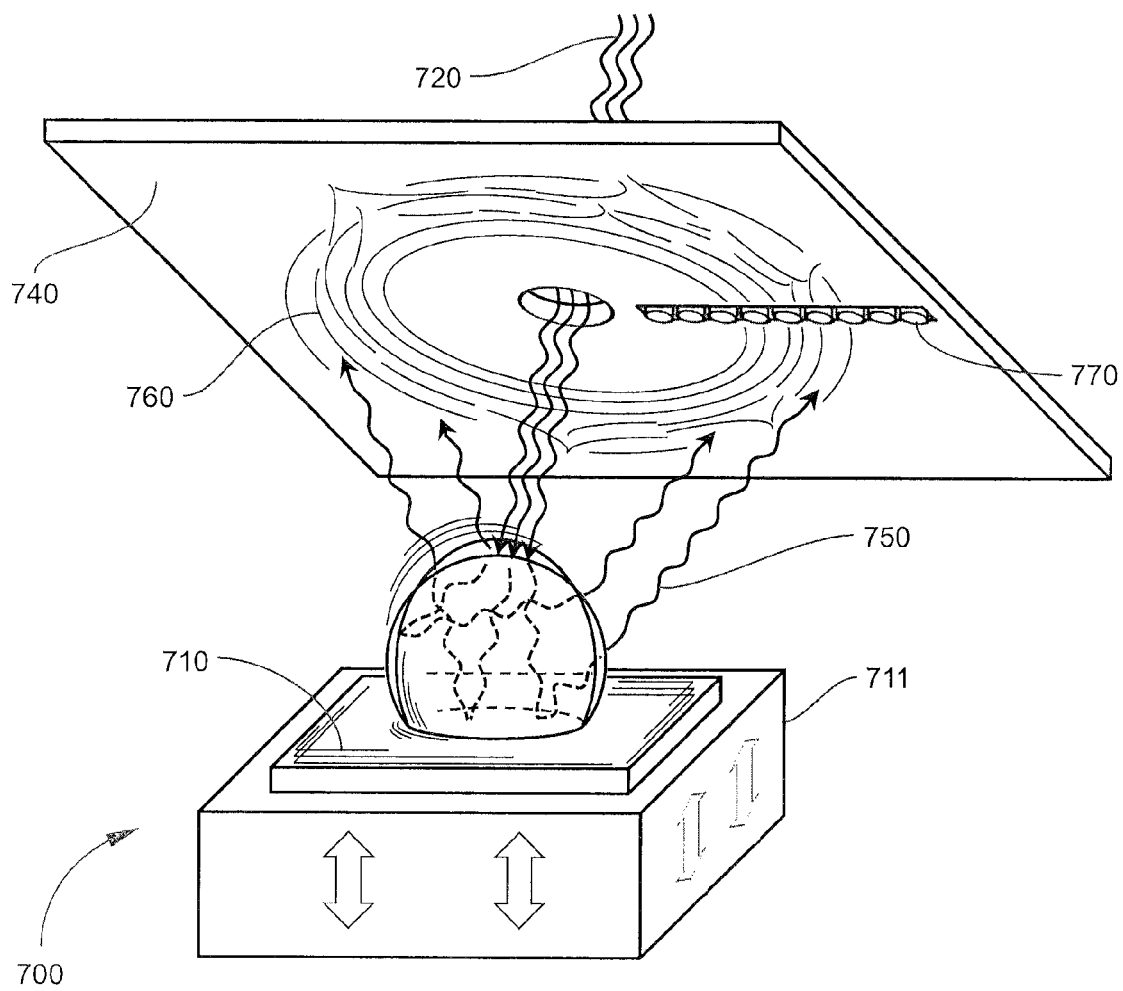
FIG. 12 illustrates a device that can be used to carry out a method according to one embodiment described herein.
Figure 13:
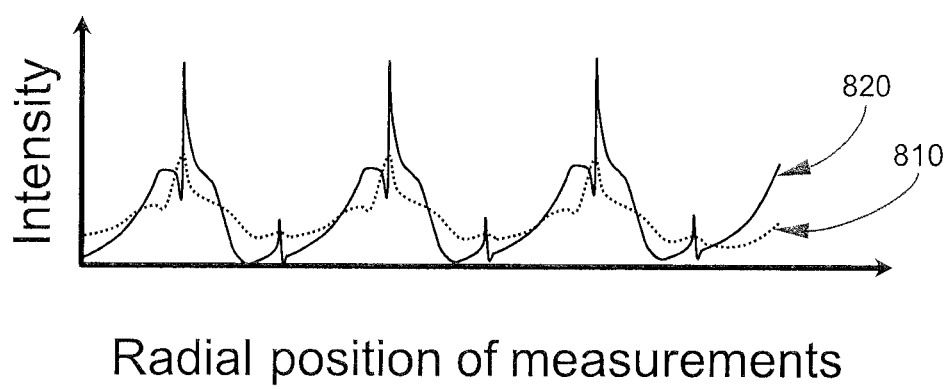
FIG. 13 illustrates data obtained by a method according to one embodiment described herein.

As illustrated by FIG. 12, a dynamic interference setup (700) can be formed which combines the interference setup (600) of FIG. 10 with a piezoelectric actuator as depicted in FIG. 7A. In the setup (700) illustrated in FIG. 12, the viewing screen (740) includes an array of photosensitive detectors (770) to measure the characteristics of the dynamic interferogram (760). Such a setup can measure the differences in vibrational characteristics of the surface (710) on which the sessile drop (100) sits and the vibrational characteristics of the dynamic interferogram (760). An example measurement from such an array is represented in FIG. 13. FIG. 13 represents the intensity as measured by the photosensitive detector when the drop is excited at a resonant frequency (810) and when the drop is excited at a non-resonant frequency (820). When fit to a geometric model of a drop as depicted in FIG. 1, the relationship between shape parameters, such as drop diameter, determined from an interference pattern and shape parameters determined from drop resonant frequency can be used to calculate additional shape parameters consistent with the geometric model.

EXAMPLE 4

Method of Determining the Shape of a Sessile Drop

Figure 14:
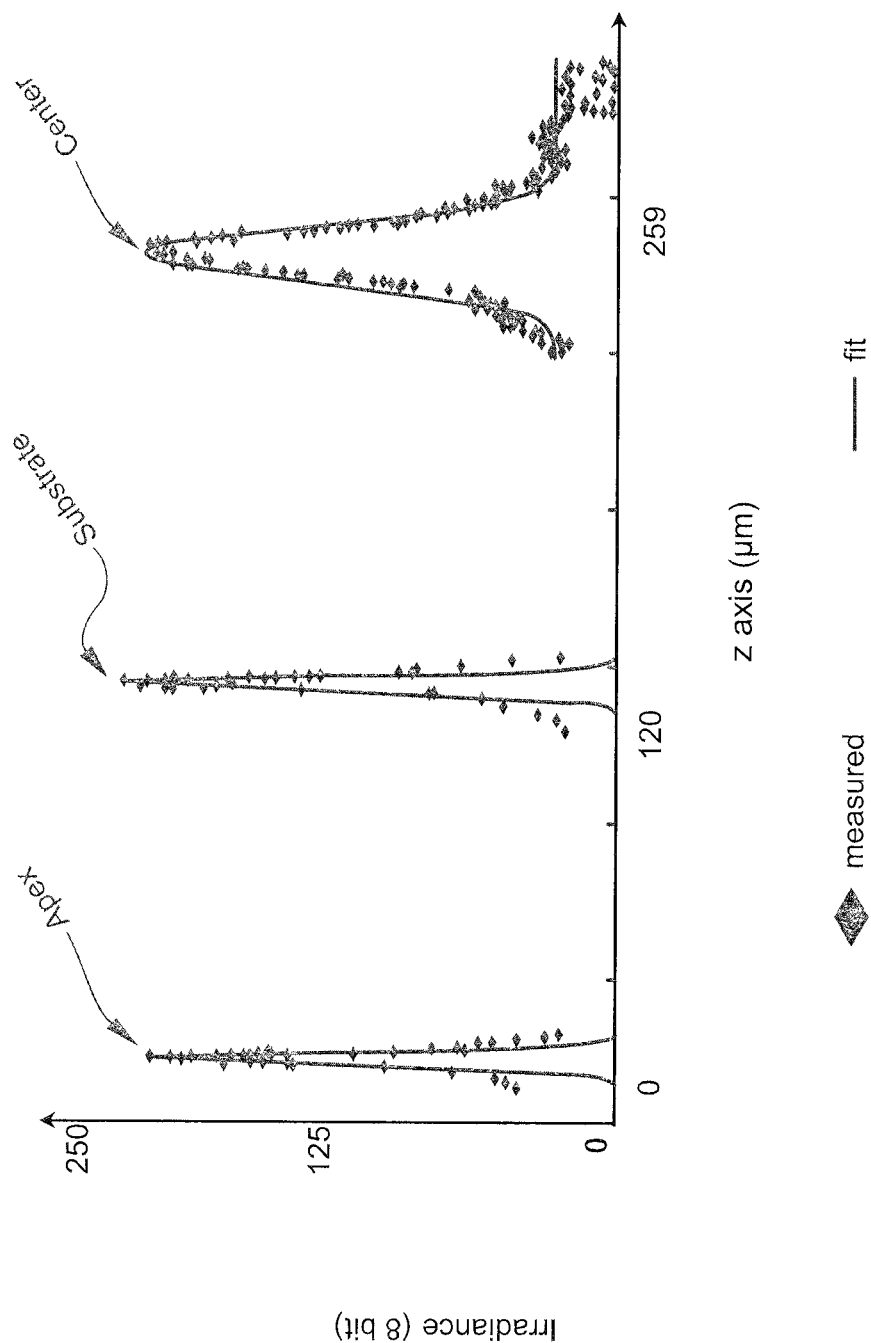
FIG. 14 illustrates data obtained by a method as according to one embodiment described herein.

In the following example, drop radius of curvature is the first shape parameter and drop height is the second shape parameter. Drop radius of curvature and drop height were determined by a radius bench technique consistent with Example 1. A 0.5 mm diameter sphere was mounted into a conical depression in a gage block to mimic a sessile drop. It is to be understood that the same principles apply to a fluid sessile drop. A fine scan was taken with a Keyence Violet Laser Color 3D Laser Scanning Microscope (Model VK-9701K), the scan consisting of 350 confocal planes, 250 through the center peak, 50 through the substrate surface, and 50 through the apex of the sphere. A minimum axial spacing between planes was 300 nm. The results of the scan are shown in FIG. 14 as a plot of the intensity values along the measurement path. To optimize signal to noise in these measurements, the laser intensity was adjusted for each feature such that the maximum measured intensity of each feature was just below the detector saturation.

A primary irradiance peak was identified which corresponded to the surface of the drop where the focal point of the confocal microscope coincided with the drop's center of curvature. A second irradiance peak was identified with a virtual, or imaginary, image of the lighting source through the instrument from the center of curvature of the object acting as a convex mirror. As shown in FIG. 14, the apex, substrate and center are identifiable. A Gaussian approximation to the point spread function was implemented consistent with Stallinga et al., "Accuracy of the Gaussian Point Spread Function model in 2D localization microscopy," *Optics express* 18.24 (2010), 24461-24476. The Gaussian curve fits for each feature are illustrated in FIG. 14.

Using this measurement process, the sample was measured seven times. After analyzing the data, the average radius of curvature of the sphere was measured to be 257.61 µm, with a standard deviation of 0.67 µm. The average height was measured to be 199.07 µm, with a standard deviation of 0.76 µm. The drop radius of curvature and drop height were fit to a geometric model corresponding to the model of FIG. 1. Wetting contact angle was then calculated according to Equation 1 hereinabove. The resultant calculated wetting contact angle was 76.870°.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of determining the shape of a sessile drop comprising:
   measuring, with a microscope, a first shape parameter of the drop to obtain a first shape parameter value, wherein the first shape parameter is drop radius of curvature;
   measuring, with the microscope, a second shape parameter of the drop to obtain a second shape parameter value, wherein the second shape parameter is drop height; and
   using the first and second shape parameter values to calculate a third shape parameter value of a third shape parameter of the drop,
   wherein the third shape parameter is drop wetting contact angle and is calculated according to Equation (1):

$$\alpha = \cos^{-1}\left(1 - \frac{h}{R}\right), \quad (1)$$

wherein α is drop wetting contact angle, h is drop height, and R is drop radius of curvature.

2. The method of claim 1, wherein the third shape parameter is a wetting contact angle of the drop on a surface.

3. The method of claim 1, wherein the first and/or second shape parameters are measured vertically.

4. The method of claim 1, wherein the first and/or second shape parameters are measured optically.

5. The method of claim 4, wherein the first and/or second shape parameters are not measured by visual inspection of the drop.

6. The method of claim 1, wherein the first and/or second shape parameters are measured from a substantially static angle.

7. A method of measuring the wettability of a surface comprising:
   disposing a sessile drop on the surface;
   measuring, with a microscope, a first shape parameter of the drop to obtain a first shape parameter value;
   measuring, with the microscope, a second shape parameter of the drop to obtain a second shape parameter value; and
   using the first and second shape parameter values to calculate a wetting contact angle of the drop on the surface,
   wherein the third shape parameter is drop wetting contact angle and is calculated according to Equation (1):

$$\alpha = \cos^{-1}\left(1 - \frac{h}{R}\right), \quad (1)$$

wherein α is drop wetting contact angle, h is drop height, and R is drop radius of curvature.

8. The method of claim 7, wherein the first shape parameter is drop radius of curvature and the second shape parameter is drop height.

9. The method of claim 8, wherein drop radius of curvature and drop height are measured by a confocal microscope.

10. The method of claim 9, wherein the drop radius of curvature is measured by radius bench confocal microscopy.

11. The method of claim 10 further comprising moving the confocal microscope laterally a distance greater than the drop radius of curvature between measuring the drop radius of curvature and measuring the drop height.

12. A method of determining the shape of a sessile drop comprising:
    measuring, with a microscope., one or more first shape parameters to obtain a geometric model of the drop;
    measuring, with the microscope, one or more second shape parameters to obtain one or more second shape parameter values; and
    using the one or more second shape parameter values to calculate one or more third shape parameter values of one or more third shape parameters,
    wherein the first, second and third shape parameters comprise all of the shape parameters of the drop, and
    wherein measuring the one or more second shape parameters comprises measuring the minimum number of second shape parameters necessary to calculate the one or more third shape parameters.

13. The method of claim 12, wherein the geometric model is a spherical model.

14. The method of claim 12, wherein the geometric model is an oblate spheroid model.

15. The method of claim 12, wherein a third shape parameter is a wetting contact angle of the drop on a surface.

16. The method of claim 15, wherein the one or more first and/or second shape parameters are not measured by visual inspection of the drop.

17. The method of claim 12, wherein the one or more first and/or second shape parameters are measured vertically.

18. The method of claim 12, wherein the one or more first and/or second shape parameters are measured optically.

19. The method of claim 12, wherein the one or more first and/or second shape parameters are measured from a substantially static angle.

20. The method of claim 12, wherein the first, second and third shape parameters of the drop are selected from the group consisting of drop height, drop radius of curvature, contact interface diameter, drop wetting contact angle, drop resonance frequency, drop optical interference pattern, drop contact angle hysteresis, drop advancing contact angle, and drop contact force.

21. A method of determining the shape of a sessile drop comprising:
    measuring, with a confocal microscope, a first shape parameter of the drop to obtain a first shape parameter value, wherein the first shape parameter is drop radius of curvature that is measured by radius bench confocal microscopy;
    moving the confocal microscope laterally a distance greater than the drop radius of curvature;

measuring, with the confocal microscope, a second shape parameter of the drop to obtain a second shape parameter value, wherein the second shape parameter is drop height; and using the first and second shape parameter values to calculate a third shape parameter value of a third shape parameter of the drop.

22. A method of determining the shape of a sessile drop comprising:

measuring, with a microscope, a first shape parameter of the drop to obtain a first shape parameter value, wherein the first shape parameter is drop resonance frequency;

measuring, with the microscope, a second shape parameter of the drop to obtain a second shape parameter value, wherein the second shape parameter is drop optical interference pattern; and using the first and second shape parameter values to calculate a third shape parameter value of a third shape parameter of the drop.

23. The method of claim 22 further comprising oscillating the drop concurrently with measuring the drop optical interference pattern.

24. A method of determining the shape of a sessile drop comprising:

measuring, with a microscope, a first shape parameter of the drop to obtain a first shape parameter value, wherein the first shape parameter is drop radius of curvature;

measuring, with the microscope, a second shape parameter of the drop to obtain a second shape parameter value, wherein the second shape parameter is drop resonance frequency; and using the first and second shape parameter values to calculate a third shape parameter value of a third shape parameter of the drop.

25. A method of measuring the wettability of a surface comprising:

disposing a sessile drop on the surface;

measuring, with a confocal microscope, a first shape parameter of the drop to obtain a first shape parameter value, wherein the first shape parameter is drop radius of curvature, and wherein the drop radius of curvature is measured by radius bench confocal microscopy;

moving the confocal microscope laterally a distance greater than the drop radius of curvature;

measuring, with the confocal microscope, a second shape parameter of the drop to obtain a second shape parameter value, wherein the second shape parameter is drop height; and using the first and second shape parameter values to calculate a wetting contact angle of the drop on the surface.

* * * * *